United States Patent [19]

Li et al.

[11] 4,065,452
[45] Dec. 27, 1977

[54] 21,21-DIHALO STEROIDS

[75] Inventors: Tsung-tee Li, Palo Alto; Michael Marx, Sunnyvale; Lewis J. Throop, Los Altos, all of Calif.

[73] Assignee: Syntex (U.S.A.) Inc., Palo Alto, Calif.

[21] Appl. No.: 711,042

[22] Filed: Aug. 2, 1976

[51] Int. Cl.$^2$ .................. C07J 71/00; A61K 31/58
[52] U.S. Cl. .................. 260/239.55 D; 424/241
[58] Field of Search .................. 260/239.55 D

[56] References Cited

U.S. PATENT DOCUMENTS 3,892,857  7/1975  Difazio et al. .............. 260/239.55 D Primary Examiner—Elbert L. Roberts
Attorney, Agent, or Firm—Tom M. Moran

[57] ABSTRACT

Novel, topically-active anti-inflammatory steroids are represented by the formula

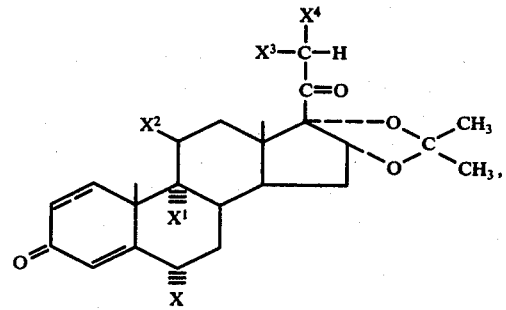

wherein X is fluoro, chloro or hydrogen; $X^1$ is fluoro, chloro, bromo, or hydrogen; $X^2$ is hydroxy or may be chloro when $X^1$ is chloro; and $X^3$ and $X^4$ are independently fluoro, chloro or bromo. These steroids are prepared by formylating at the 21-position a 16α,17β-isopropylidenedioxypregna-1,4,9(11)-triene-3,20-dione or the corresponding 21-fluoro compound, halogenating at the 21 position, deformylating, then reacting to add the desired components at the 9α and 11β positions.

29 Claims, No Drawings

21,21-DIHALO STEROIDS

BACKGROUND OF THE INVENTION

1. Field of the Invention

This invention relates to a new class of 16α,17α-acetonide steroids which are 21,21-dihalo substituted. More specifically they are compounds which are 21,21-dihalo-16α, 17α-isopropylidenedioxypregna-1,4-diene-3,20-diones and the corresponding pregn-4-enes which may have a 6α-halo substituent, a 9α-fluoro or chloro substituent, and an 11β-hydroxy substituent or 11β-chloro substituent. The compounds of the invention are useful as topical anti-inflammatories. The invention also relates to a process for making the compounds of this invention which comprises formylating at the 21 position a $\Delta^{1,4,9(11)}$ steroid having either one halo substituent or no halo substituents at the 21 position, halogenating, subsequently deformylating, and reacting at the 9(11) double bond to form the compounds of the invention.

2. Prior Art

It is known from U.S. Pat. No. 3,236,866 to Ringold and Edwards that 21,21-difluoro-$\Delta^1$-pregnenes are useful as progestational agents and as such exhibit anti-androgenic, anti-estrogenic and anti-gonadotrophic activity. It is also known from U.S. Pat. No. 3,681,405 patented Aug. 1, 1972 to Laurent et al. that certain 21,21-dichloro steroids have anti-inflammatory activity. The compounds are represented by the formula

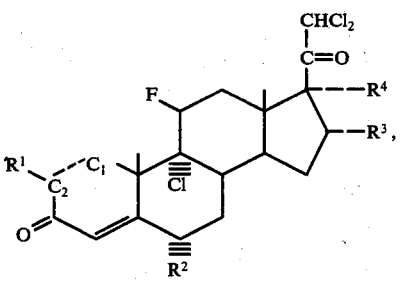

wherein
$R^1$ is hydrogen or chlorine;
$R^2$ is hydrogen, fluorine or methyl;
$R^3$ is hydrogen or methyl;
$R^4$ is hydrogen or a free or esterified hydroxy group; and
$C_1 = C_2$ represents a single or double bond joining carbon atoms at the 1 and 2 position.

It is further known that 21,21-diiodo, -dibromo, and dichloro steroids are useful as intermediates in preparation of certain steroid compounds. See for example Canadian Pat. No. 769,025; French Pat. No. 1,243,528; U.S. Pat. No. 2,715,621; U.S. Pat. No. 2,752,366; and German Pat. No. DT2225658, the latter patent disclosing the 21,21-diiodo compounds which are useful for the preparation of triamcinalone, fluocinolone, dexamethasone, betamethasone, and paramethasone.

SUMMARY OF THE INVENTION

One aspect of this invention is a compound selected from those represented by the formula

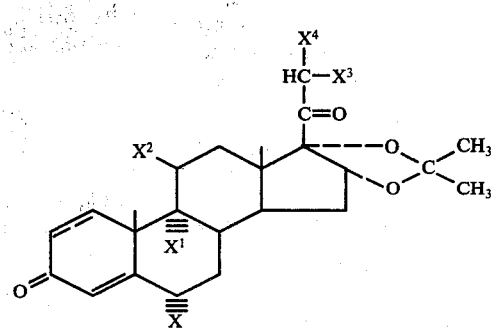

wherein
X is fluoro, chloro or hydrogen;
$X^1$ is hydrogen, fluoro, chloro or bromo;
$X^2$ is hydroxy or may be chloro when $X^1$ is chloro;
$X^3$ and $X^4$ are independently fluoro, chloro, or bromo; and
the broken line between C-1 and C-2 indicates that the bond between C-1 and C-2 is a single or a double bond. Of the compounds encompassed by the generic formula, the preferred compound is selected from those represented by formula (I) wherein $X^3$ and $X^4$ are independently fluoro or chloro and X, $X^1$, $X^2$ and the broken line are as previously defined.

Another aspect of this invention is a method of treating an inflamed condition in mammals which method comprises topically applying at least one compound to the inflamed condition.

Still another aspect of the invention is the anti-inflammatory combination of at least one compound of this invention with a suitable, pharmaceutically acceptable carrier.

Another aspect of this invention is a process which comprises a. reacting a formylating agent with a compound represented by the formula

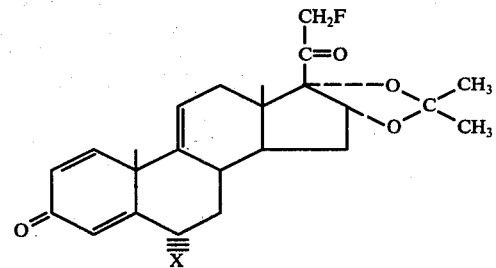

wherein X is fluoro, chloro or hydrogen, to form a compound represented by the formula

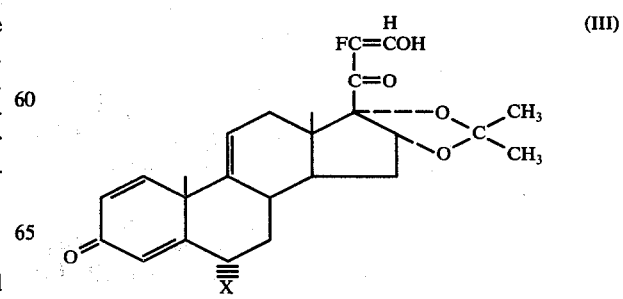

wherein X is previously defined;

b. reacting the compound represented by formula (III) with a halogenating agent to form a compound represented by the formula

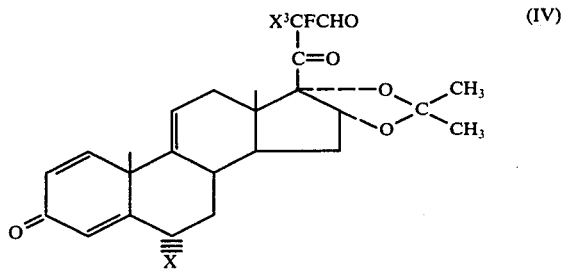

(IV)

wherein X is previously defined and $X^3$ is chloro or bromo c. reacting the compound represented by formula (IV) with a deformylating agent to form a compound represented by the formula

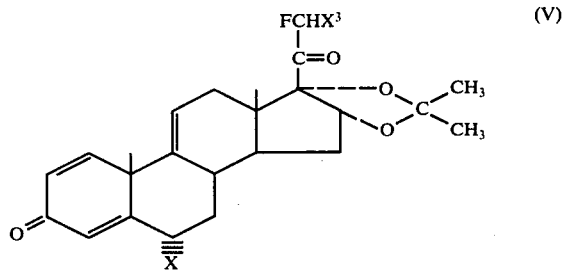

(V)

wherein X and $X^3$ are defined previously d. treating the compound of formula (V) with a suitable reactant or reactants, as described hereinafter, to form a 21-fluoro-21-halo compound of this invention represented by formula (I) wherein X, $X^1$, $X^2$ and $X^3$ are previously defined; and e. optionally, if the $\Delta^4$ steroids of the invention are desired, reducing the $C_1 - C_2$ double to a single bond.

Alternatively, the $\Delta^4$ steroids may be obtained by proceeding through steps (a)-(d) but substituting and ethylene ketal derivative for the compound represented by formula (II), namely a compound represented by

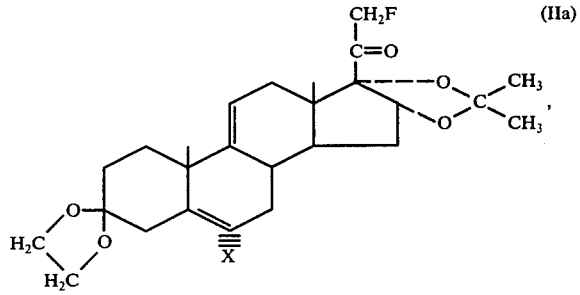

(IIa)

then hydrolyzing the ketal to form a 21-fluoro-21-halo-$\Delta^4$ steroid of formula (I). The $\Delta^{1,4}$ steroid of formula (I) is thereafter obtained by forming an unsaturated bond between $C_1$ and $C_2$ as discussed hereafter The 21,21-difluoro steroids of the invention are obtained by reacting a compound represented by formula (IV) with a fluorinating agent to substitute a fluoro for the $X^3$ group at the 21 carbon.

The 21,21-dichloro or 21,21-dibromo steroids of the invention are prepared by a. formylating an appropriate 16α,17α-isopropylidenedioxypregna-1,4,9(11)-triene-3,20-dione to form the corresponding compound having a hydroxymethylene group at the 21 position;

b. halogenating the product from the previous step to form the corresponding 21,21-dihalo-21-formyl-steroid;

c. deformylating to form the corresponding 21,21-dihalo compound;

d. treating the resulting product to add the desired substituents at 9α-and 11β-positions; and e. optionally, reducing the $\Delta^1$ bond.

The 21-bromo-21-chloro steroids are similarly prepared except that in step (b) immediately above, the compound is chlorinated (or brominated) to give the 21-chloro (or 21-bromo)-21-formyl steroid then brominated (or chlorinated) to give the 21-chloro-21-bromo-21-formyl steroid.

FURTHER DESCRIPTION OF THE INVENTION AND PREFERRED EMBODIMENTS

Compounds of the Invention

Compounds falling within the scope of the invention are those represented by formula (I) wherein X is hydrogen, fluoro, or chloro;

$X^1$ is hydrogen, fluoro, chloro or bromo;

$X^2$ is hydroxy or may be chloro when $X^1$ is chloro;

$X^3$ and $X^4$ are independently fluoro, chloro or bromo; and the broken line between C-1 and C-2 represents a single or a double bond. Thus compounds failling within the scope of the claims include the following compounds which are named as 16α,17α-isopropylidenedioxypregna-1,4-diene-3,20-diones or 16α,17α-isopropylidenedioxypregn-4-ene-3,20-diones, with the substituents on the 6α-,9α-,11β-,21-positions being named in alphabetical order:

$\Delta^{1,4}$ Steroids

6α,21,21-trifluoro-11β-hydroxy-16α,17α-isopropylidenedioxypregna-1,4-diene-3,20-dione;

21-chloro-6α,21-difluoro-11β-hydroxy-16α,17α-isopropylidenedioxypregna-1,4-diene-3,20-dione;

21-bromo-6α,21-difluoro-11β-hydroxy-16α,17α-isopropylidenedioxypregna-1,4-diene-3,20-dione;

21,21-dichloro-6α-fluoro-11β-hydroxy-16α,17α-isopropylidenedioxypregna-1,4-diene-3,20-dione;

21-bromo-21-chloro-6α-fluoro-11β-hydroxy-16α,17α-isopropylidenedioxypregna-1,4-diene-3,20-dione;

21,21-dibromo-6α-fluoro-11β-hydroxy-16α,17α-isopropylidenedioxypregna-1,4-diene-3,20-dione;

6α,9α,21,21-tetrafluoro-11β-hydroxy-16α,17α-isopropylidenedioxypregna-1,4-diene-3,20-dione;

21-chloro-6α,9α,21-trifluoro-11β-hydroxy-16α,17α-isopropylidenedioxypregna-1,4-diene-3,20-dione;

21-bromo-6α,9α,21-trifluoro-11β-hydroxy-16α,17α-isopropylidenedixoypregna-1,4-diene-3,20-dione;

21,21-dichloro-6α,9α-difluoro-11β-hydroxy-16α,17α-isopropylidenedioxypregna-1,4-diene-3,20-dione;

21-bromo-21-chloro-6α,9α-difluoro-11β-hydroxy-16α,17α-isopropylidenedioxypregna-1,4-diene-3,20-dione;

21,21-dibromo-6α,9α-difluoro-11β-hydroxy-16α,17α-isopropylidenedioxypregna-1,4-diene-3,20-dione;

9α-chloro-6α,21,21-trifluoro-11β-hydroxy-16α,17α-isopropylidenedioxypregna-1,4-diene-3,20-dione;
9α,21-dichloro-6α,21-difluoro-11β-hydroxy-16α,17α-isopropylidenedioxypregna-1,4-diene-3,20-dione;
21-bromo-9α-chloro-6α,21-difluoro-11β-hydroxy-16α,17α-isopropylidenedioxypregna-1,4-diene-3,20-dione;
9α,21,21-trichloro-6α-fluoro-11β-hydroxy-16α,17α-isopropylidenedioxypregna-1,4-diene-3,20-dione;
6α,21,21-trifluoro-9α,11β-dichloro-16α,17α-isopropylidenedioxypregna-1,4-diene-3,20-dione;
9α,11β,21-trichloro-6α,21-difluoro-16α,17α-isopropylidenedioxypregna-1,4-diene-3,20-dione;
21-bromo-9α,11β-dichloro-6α,21-difluoro-16α,17α-isopropylidenedioxypregna-1,4-diene-3,20-dione;
9α,11β,21,21-tetrachloro-16α,17α-isopropylidenedioxypregna-1,4-diene-3,20-dione;
6α-chloro-21,21-difluoro-11β-hydroxy-16α,17α-isopropylidenedioxypregna-1,4-diene-3,20-dione;
6α,21-dichloro-21-fluoro-11β-hydroxy-16α,17α-isopropylidenedioxypregna-1,4-diene-3,20-dione;
21-bromo-6α-chloro-21-fluoro-11β-hydroxy-16α,17α-isopropylidenedioxypregna-1,4-diene-3,20-dione;
6α,21,21-trichloro-11β-hydroxy-16α,17α-isopropylidenedioxypregna-1,4-diene-3,20-dione;
6α-chloro-9α,21,21-trifluoro-11β-hydroxy-16α,17α-isopropylidenedioxypregna-1,4-diene-3,20-dione;
6α,21-dichloro-9α,21-difluoro-11β-hydroxy-16α,17α-isopropylidenedioxypregna1,4-diene-3,20-dione;
21-bromo-6α-chloro-9α,21-difluoro-11β-hydroxy-16α,17α-isopropylidenedioxypregna-1,4-diene-3,20-dione;
6α,21,21-trichloro-9α-fluoro-11β-hydroxy-16α,17α-isopropylidenedioxypregna-1,4-diene-3,20-dione;
6α,9α-dichloro-21,21-difluoro-11β-hydroxy-16α,17α-isopropylidenedioxypregna-1,4-diene-3,20-dione;
6α,9α,21-trichloro-21-fluoro-11β-hydroxy-16α,17α-isopropylidenedioxypregna-1,4-diene-3,20-dione;
21-bromo-6α,9α-dichloro-21-fluoro-11β-hydroxy-16α,17α-isopropylidenedioxypregna-1,4-diene-3,20-dione;
6α,9α,21,21-tetrachloro-11β-hydroxy-16α,17α-isopropylidenedioxypregna-1,4-diene-3,20-dione;
6α,9α,11β-trichloro-21,21-difluoro-16α,17α-isopropylidenedioxypregna-1,4-diene-3,20-dione;
6α,9α,11β,21-tetrachloro-21-fluoro-16α,17α-isopropylidenedioxypregna-1,4-diene-3,20-dione;
21-bromo-6α,9α,11β-trichloro-21-fluoro-16α,17α-isopropylidenedioxypregna-1,4-diene-3,20-dione;
6α,9α,11β,21,21-pentachloro-16α,17α-isopropylidenedioxypregna-1,4-diene-3,20-dione;
9α,21,21-trifluoro-11β-hydroxy-16α,17α-isopropylidenedioxypregna-1,4-diene-3,20-dione;
21-chloro-9α,21-difluoro-11β-hydroxy-16α,17α-isopropylidenedioxypregna-1,4-diene-3,20-dione;
21,21-dichloro-9α-fluoro-11β-hydroxy-16α,17α-isopropylidenedioxypregna-1,4-diene-3,20-dione;
9α,11β-dichloro-21,21-difluoro-16α,17α-isopropylidenedioxypregna-1,4-diene-3,20-dione;
9α,11β,21-trichloro-21-fluoro-16α,17α-isopropylidenedioxypregna-1,4-diene-3,20-dione;
9α,11β,21,21-tetrachloro-16α,17α-isopropylidenedioxypregna-1,4-diene-3,20-dione;
9α-bromo-6α,21,21-trifluoro-11β-hydroxy-16α,17α-isopropylidenedioxypregna-1,4-diene-3,20-dione;
9α-bromo-6α-chloro-21,21-difluoro-11β-hydroxy-16α,17α-isopropylidenedioxy-1,4-diene-3,20-dione;
9α-bromo-21,21-difluoro-11β-hydroxy-16α,17α-isopropylidenedioxypregna-1,4-diene-3,20-dione;
9α-bromo-21-chloro-6α,21-difluoro-11β-hydroxy-16α,17α-isopropylidenedioxypregna-1,4-diene-3,20-dione;
9α-bromo-21,21-dichloro-6α-fluoro-11β-hydroxy-16α,17α-isopropylidenedioxypregna-1,4-diene-3,20-dione;
9α-bromo-6α,21,21-trifluoro-11β-hydroxy-16α,17α-isopropylidenedioxypregna-1,4-diene-3,20-dione;
21,21-difluoro-11β-hydroxy-16α,17α-isopropylidenedioxypregna-1,4-diene-3,20-dione;
9α-bromo-21-chloro-21-fluoro-11β-hydroxy-16α,17α-isopropylidenedioxypregna-1,4-diene-3,20-dione;
21,21-dichloro-6α-fluoro-11β-hydroxy-16α,17α-isopropylidenedioxypregna-1,4-diene-3,20-dione;

Δ⁴ Steroids 21,21-dichloro-6α,9α-difluoro-11β-hydroxy-16α,17α-isopropylidenedioxypregn-4-ene-3,20-dione;
21-bromo-21-chloro-6α,9α-difluoro-11β-hydroxy-16α,17α-isopropylidenedioxypregn-4-ene-3,20-dione;
6α,21,21-trifluoro-9α-chloro-11β-hydroxy-16α,17α-isopropylidenedioxypregn-4-ene-3,20-dione;
21-bromo-9α-chloro-6α,21-difluoro-11β-hydroxy-16α,17α-isopropylidenedioxypregn-4-ene-3,20-dione;
9α,21-21-trichloro-6α-fluoro-11β-hydroxy-16α,17α-isopropylidenedioxypregn-4-ene-3,20-dione;
6α,21,21-trifluoro-9α,11β-dichloro-16α,17α-isopropylidenedioxypregn-4-ene-3,20-dione;
9α,11β,21-trichloro-6α-21-difluoro-16α,17α-isopropylidenedioxypregn-4-ene-3,20-dione;
21-bromo-9α,11β-dichloro-6α,21-difluoro-16α,17α-isopropylidenedioxypregn-4-ene-3,20-dione;
9α,11β-21,21-tetrachloro-16α,17α-isopropylidenedioxypregn-4-ene-3,20-dione;
6α-chloro-21,21-difluoro-11β-hydroxy-16α,17α-isopropylidenedioxypregn-4-ene-3,20-dione;
6α,21-dichloro-21-fluoro-11β-hydroxy-16α,17α-isopropylidenedioxypregn-4-ene-3,20-dione;
6α-chloro-9α,21,21-trifluoro-11β-hydroxy-16α,17α-isopropylidenedioxypregn-4-ene-3,20-dione;
6α,21-dichloro-9α,21-difluoro-11β-hydroxy-16α,17α-isopropylidenedioxypregn-4-ene-3,20-dione;
21-bromo-6α-chloro-9α,21-difluoro-11β-hydroxy-16α,17α-isopropylidenedioxypregna-4-ene-3,20-dione;
6α,21,21-trichloro-9α-fluoro-11β-hydroxy-16α,17α-isopropylidenedixoypregn-4-ene-3,20-dione;
6α,9α-dichloro-21,21-difluoro-11β-hydroxy-16α,17α-isopropylidenedioxypregn-4-ene-3,20-dione;
6α,9α,21-trichloro-21-fluoro-11β-hydroxy-16α,17α-isopropylidenedioxypregn-4-ene-3,20-dione;
21-bromo-6α,9α-dichloro-21-fluoro-11β-hydroxy-16α,17α-isopropylidenedioxypregn-4-ene-3,20-dione;
6α,9α,21,21-tetrachloro-11β-hydroxy-16α,17α-isopropylidenedioxypregn-4-ene-3,20-dione;
6α,9α,11β-trichloro-21,21-difluoro-16α,17α-isopropylidenedioxypregn-4-ene-3,20-dione;

6α,9α-11β-21-tetrachloro-21-fluoro-16α,17α-isopropylidenedioxypregn-4-ene-3,20-dione;

6α-bromo-21-chloro-9α,21-difluoro-11β-hydroxy-16α,17α-isopropylidenedioxypregna-4-ene-3,20-dione;

6α,21,21-trifluoro-11β-hydroxy-16α,17α-isopropylidenedioxypregn-4-ene-3,20-dione;

21-chloro-6α,21-difluoro-11β-hydroxy-16α,17α-isopropylidenedioxypregn-4-ene-3,20-dione;

21,21-dichloro-6α-fluoro-11β-hydroxy-16α,17α-isopropylidenedioxypregn-4-ene-3,20-dione;

6α,9α-21,21-tetrafluoro-11β-hydroxy-16α,17α-isopropylidenedioxypregn-4-ene-3,20-dione;

21-chloro-6α,9α,21-trifluoro-11β-hydroxy-16α,17α-isopropylidenedioxypregn-4-ene-3,20-dione; and other Δ⁴ steroids corresponding to the Δ¹,⁴ steroids named hereinbefore.

Of the compounds broadly set forth above, the group that is particularly valuable and therefore preferred includes the compounds represented by formula (I) wherein $X^3$ and $X^4$ are each independently chosen from fluoro or chloro and X, $X^1$, $X^2$ and the broken line between $C_1$ and $C_2$ are as described in this section hereinbefore. An especially preferred subgroup is that wherein X is fluoro; $X^1$ is fluoro or chloro; $X^3$ is fluoro; $X^4$ is fluoro or chloro; and $X^2$ is as previously described.

Process For Preparation

The essence of the process aspect of this invention is premised on the discovery that certain known 16α,17α-isopropylidenedioxypregna-1,4,9(11)-triene-3,20-diones compounds which are substituted by one fluoro atom at the 21 position or have no fluoro at the 21 position can be 21-formylated, halogenated and deformylated to form novel intermediates from which the novel anti-inflammatory compounds of this invention are obtained. Reaction Scheme A exemplifies one facet of the process for preparing the compounds of this invention. In this reaction scheme the wavy line indicates that the rest of the steroid molecule remains unchanged.

REACTION SCHEME A

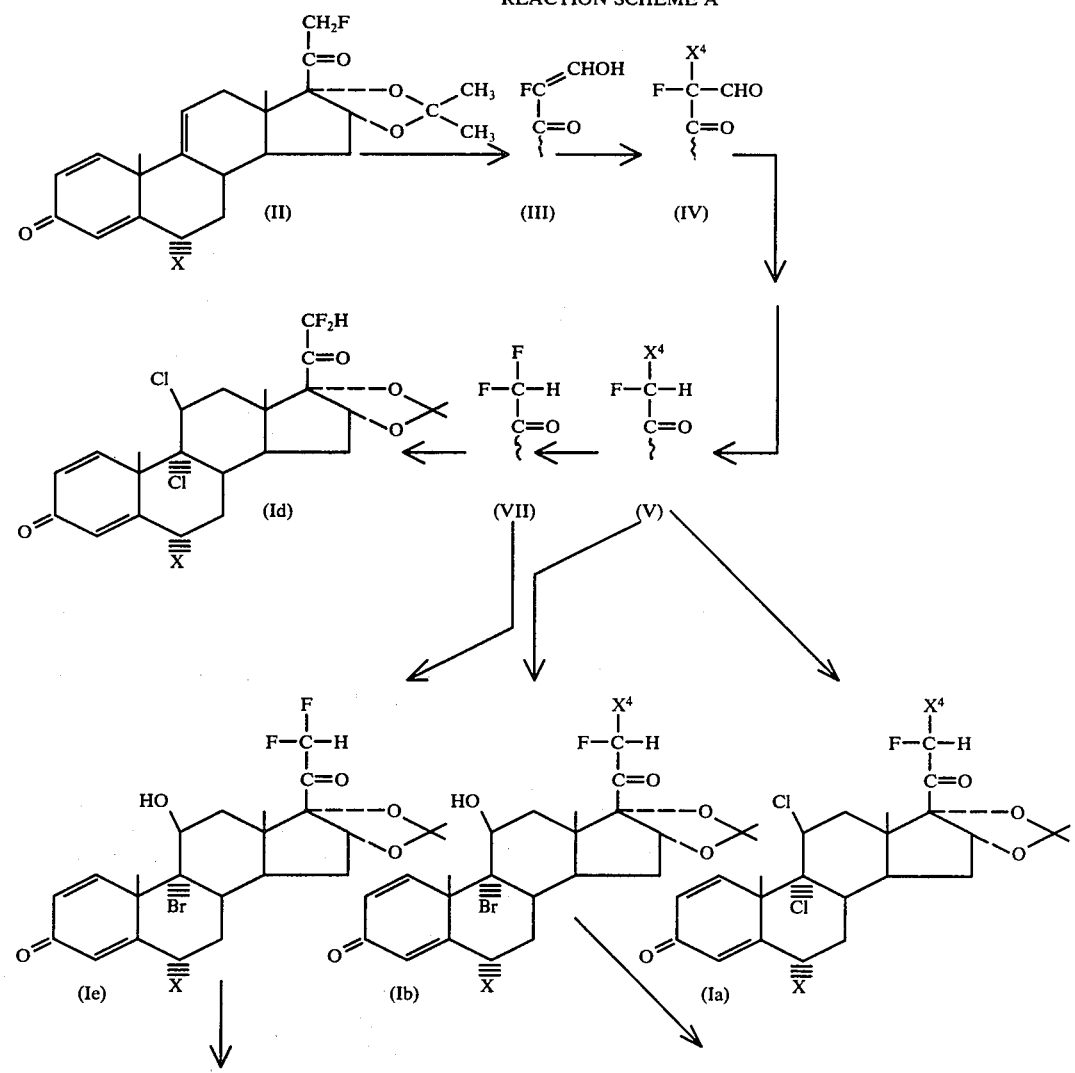

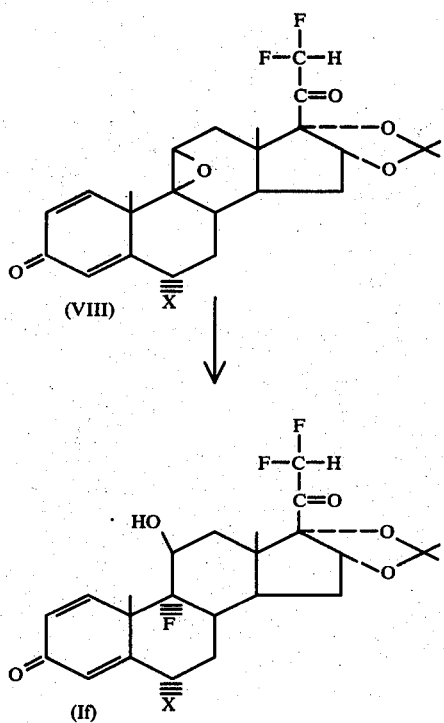

(VIII)

(If)

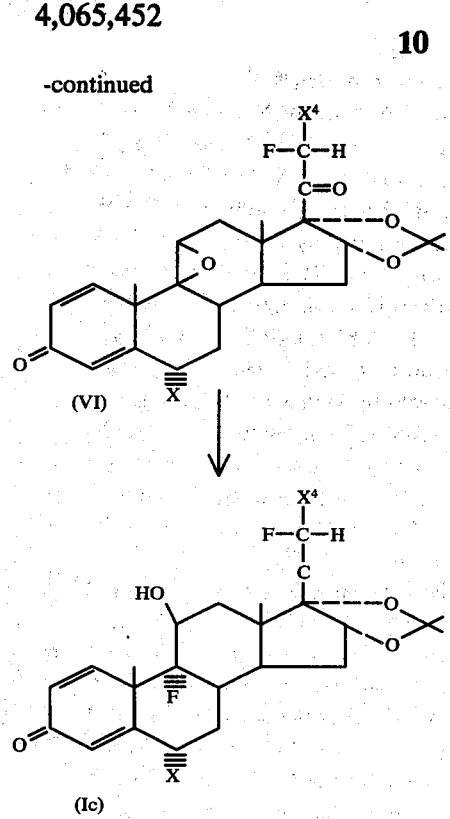

(VI)

(Ic)

One aspect of the process of this invention comprises (a) treating a compound (II) which is substituted with a fluorine atom on the 21 carbon of the steroid chain with a formylating agent to form a compound of formula (III), (b) treating the compound of formula (III) with a suitable halogenating agent to form a 21-fluoro-21-halo compound (IV) also having a formyl group attached to $C_{21}$; and (c) deformylating the compound, i.e., the formyl group is removed to form a compound indicated as formula (V).

The compound of formula (V) may be treated with a suitable chlorinating agent to form a compound of formula (Ia), or may be treated to form a $9\alpha,11\beta$-bromhydrin of formula (Ib) which in turn is epoxidized then hydrofluorinated to form a $9\alpha,11\beta$-fluorhydrin of this invention represented by formula (Ic).

a. In the first step of the process of this invention the starting material, a $16\alpha,17\alpha$-isopropylidenedioxypregna-1,4,9(11)-triene-3,20-dione which is substituted at the 21 position with a fluoro substituent, and preferably with a $6\alpha$-fluoro or $6\alpha$-chloro substituent, and preferably with a $6\alpha$-fluoro or $6\alpha$-chloro substituent is mixed with a suitable hindered base such as N-isopropyl-N-lithium-cyclohexylamine (formed by reacting isopropylcyclohexylamine with n-alkyl lithium in an appropriate aprotic solvent such as a mixture of tetrahydrofuran and hexametylphosphoric triamide or other suiable ethers such as glyme, dioxane, tetrahydropyran (THP), and the like), N-lithium-diisopropylamine, N-lithium bis-1,1,1-trimethylsilylamine. The reactants are stirred together preferably in an inert atomosphere such as nitrogen or argon at temperatures from about 10° to 50° C preferably at about 20°–25° C for 5 to 24 hours. A suitable formylating agent such as ethyl formate is added and the reaction continued for a time sufficient to form a compound represented by formula (III). Generally this will be about 2 to 10 hours, preferably about 4 or 5 hours. The resulting product can then be extracted and crystallized using methods well known in the art for this particular process.

b. Once a reaction product represented by formula (III) is obtained, it is reacted with at least an equimolar amount of a halogenating agent, i.e. (i) a suitable chlorinating agent such as copper chloride with lithium chloride, t-butyl hypochlorite, sulfuryl chloride and the like, (ii) a suitable brominating agent such as cupric bromide and the like or (iii) a suitable fluorinating agent such as trifluoromethyl hypofluorite, perchloryl fluoride, and the like, in a suitable solvent such as DMF, chloroform, THF, and the like. Generally the reaction will take place at a temperature of about 25° to 100° C, preferably about 40° to 50° C for the first part of the reaction then 70° to 90° C for the latter part of the reaction. The reaction will be completed in about 2 to 10 hours, preferably about 3 hours at the lower temperature and 1 hour at the upper temperature.

c. The resulting 21-fluoro-21-chloro (21-bromo or 21-difluoro)-21-formyl steroid (IV) is reacted with a molar excess of a deformylating agent such as an alkali metal hydroxide (e.g. sodium or potassium hydroxide), an alkaline earth hydroxide (e.g. barium hydroxide), and the like in a suitable solvent such as ethanol, methanol, ether, water, and the like or mixtues thereof. This reaction will take place generally at about −10° to +10° C, preferably at 0° C for a period of time sufficient to complete the reaction which is generally about 1 to 5 hours, preferably about 2 to 3. Purification and recrystallization can be done using procedures known in the art.

An alternative method for preparing a 21,21-difluorosteroid such as (Id), (Ie) or (If) is to treat the resulting product if a 21-bromo or 21-chloro is present, with a suitable fluorinating agent such as tetramethylammonium fluoride in an appropriate solvent such as sulfolane at the appropriate tenperature, for example about 40° to 120° C, preferably about 70° to 90° C for a period of time sufficient to complete the reaction, i.e. generally about 2 to 10 hours, preferably about 2 to 3. After purification the resulting 21,21-difluoro compound (VI) (or the 21,21-mixed halogen compound) is further treated to form the corresponding 9α,11α-dichloro compound represented by formula (Id) (or formula (Ia) in the case of the 21,21-mixed halogen compound) by chlorinating across the double bond between C-9 and C-11. The chlorination step may be carried out using procedures known in the art, e.g. see "Steroids" 5, 615–35 (1965) by Heller et al. Generally chlorine gas is bubbled through a solution of the reactant in a chlorinated hydrocarbon such as methylene dichloride in the presence of a suitable base catalyst such as pyridine. Generally the addition takes no more than a few minutes at about 20°–30° C.

A 9α-fluoro-11β-hydroxy compound represented by formulae (Ic) or (If) is formed by epoxidizing the bond between the C-9 and C-11 carbons in formulae (V) or (VII). The epoxidation is a two step procedure wherein a compound of this invention represented by formulae (Ib) or (Ie) is prepared by reacting (V) or (VII) with dibromantin along with a dilute perchloric acid solution. In this step, an intermediate having 9α-bromo-11β-hydroxy substituents on the steroid structure (Ib) or (Ie) is first formed which may be readily purified using procedures well known in the art. This material (either crude or pure) is then dehydrobrominated using for example isopropyl alcohol and potassium acetate at reflux temperature for a time sufficient to form the epoxide as indicated in formulae (VI) and (VIII).

The resulting epoxide compound is purified then reacted with a hydrohalogenating agent such as hydrofluoric or hydrochloric acid to form a 9α-halo-11β-hydroxy compound of this invention. Such hydrohalogenating procedures are well known in the art. See for example *Organic Reactions In Steroid Chemistry*, Vol. I, edited by J. Fried and J. Edwards, Chap. 8, Van Nostrand Rheinhold (1972), which is incorporated herein by reference.

By reacting the compounds represented by formulae (Ib) and (Ie) with, e.g., tributyltin hydride in a suitable solvent such as THF, other compounds of the invention represented by the following formulae may be respectively obtained:

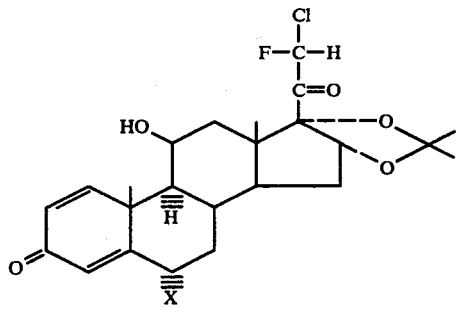
(Ib')

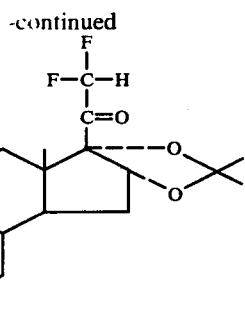
(Ie')

Generally the conversion is implemented by irradition in the presence of azobisisobutyronitrile.

The 21,21-dichloro, 21-bromo-21-chloro and 21,21-dibromo steroids of the invention are prepared by a process similar to that set forth in Reaction Scheme A, but instead of a 21-fluoro steroid as a starting material, a 16α,17α-isopropylidenedioxypregna-1,4,9(11)-triene-3,20-dione is employed as set forth in Reaction Scheme B. In this reaction scheme the wavy lines in formulae (IIIB), (IIIC), (IVB) and (VB) indicate that the remainder of the steroid structure (i.e. positions 1–19) is the same as that depicted in formula (IIB).

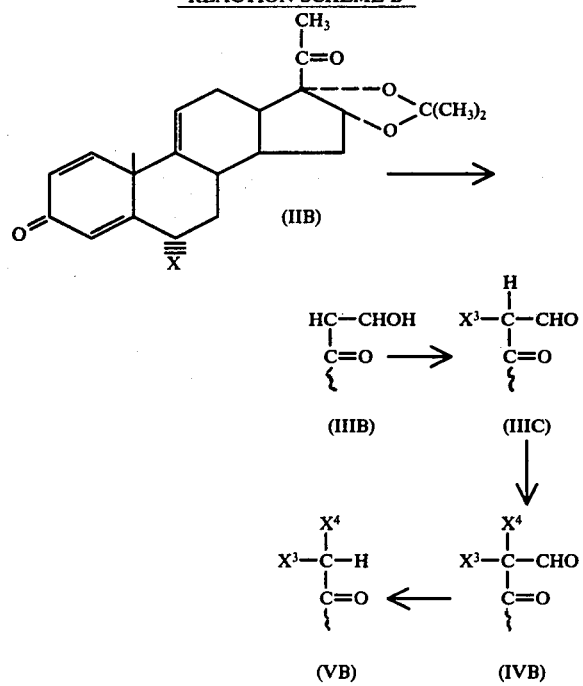

The starting material represented by (IIB) is formylated under substantially similar conditions described for the first step in Reaction Scheme A, supra, except that the reaction is carried out at reflux conditions. The 21-formylated steroid (IIIB) is then halogenated, that is chlorinated or brominated, by reacting the compound represented by formula (IIIB) with a suitable halogenating agent in an appropriate inert solvent at temperatures of about 0° to 100° C, depending on the reactants and solvents, to give the 21,21-dihalo steroid of formula (IVB). Suitable chlorinating agents include cupric chloride with lithium chloride, sulfuryl chloride, t-butyl hypochlorite, and the like, preferably cupric chloride with lithium chloride, while suitable brominating agents include cupric bromide, N-bromosuccinimide, bromine, and the like, preferably cupric bromide. Appropriate solvents include dimethylformamide, ethyl acetate, chloroform, carbon tetrachloride, and the like and may be used for either the chlorination or bromination.

If the 21,21-dichloro or 21,21-dibromo steroid is desired, then at least two molar equivalents of the chlorinating agent or brominating agent must be respectively used to give a compound represented by formula (IVB) wherein $X^3$ and $X^4$ are both chloro or both bromo. If, on the other hand, the 21-bromo-21-chloro-steroid is desired, the halogenation is carried out stepwise by first reacting about an equimolar amount of a chlorinating (or brominating) agent with a compound represented by formula (IIIB) to give a 21-chloro (or bromo) compound represented by formula (IIIC) and thereafter brominating (or chlorinating) the resulting compound of formula (IIIC) to give (IVB) wherein $X^3$ is chloro and $X^4$ is bromo. The resulting 21,21-dichloro-21-formyl; 21,21-dibromo-21-formyl; or 21-bromo-21-chloro-21-formyl steroids may be purified by methods known in the art such as solvent extraction and evaporation, filtration, recrystallization, and the like.

The steroid represented by formula (IVB) is then deformylated according to the procedure discussed hereinbefore in relation to Reaction Scheme A to form a 21,21-dihalo-16α,17α-isopropylidenedioxypregna-1,4,9(11)-triene, 3,20-dione represented by formula (VB). This in turn is reacted according to procedures set forth supra to form $\Delta^{1,4}$ steroids of this invention represented by formula (I) wherein $X^3$ and $X^4$ are independently chloro or bromo; the broken line between $C_1-C_2$ represents a double bond; and $X^1$ and $X^2$ are previously defined.

The $\Delta^4$ steroids of this invention are then easily obtained by reducing the $C_1-C_2$ double bond of the $\Delta^{1,4}$ steroids using a suitable reducing agent such as hydrogen with an appropriate catalyst such as tris-(triphenylphosphine)chlororhodium in an acceptable inert solvent such as a mixture of benzene and ethanol. Such a reaction readily takes place at 0° to 50° C, with 20° to 25° C being preferred.

Alternatively, the $\Delta^4$ steroids of this invention represented by formula (I) wherein the bond between $C_1$ and $C_2$ is a single bond may be prepared by first forming an ethylene ketal derivative of the $\Delta^{4,9(11)}$ analog of a compound represented by formula (II) or (IIB), viz

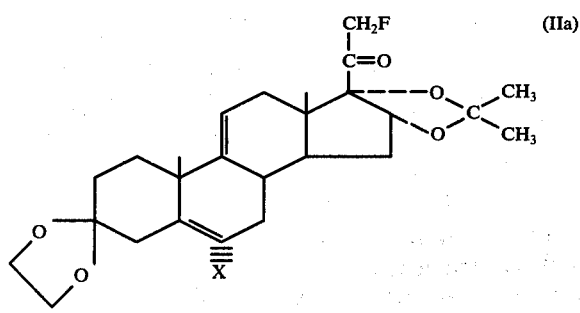

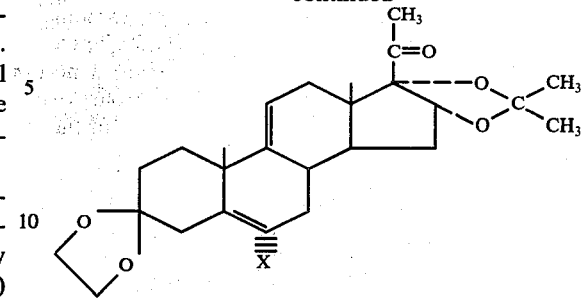

then going through the steps discussed hereinbefore in relation to Reaction Schemes A and B to arrive at the ethylene ketal derivatives represented by the formula

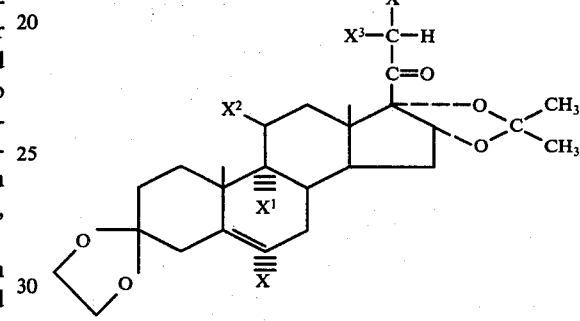

wherein

X, $X^1$, $X^2$, $X^3$ and $X^4$ are defined previously. These compounds are then hydrolyzed to form compounds of this invention. The hydrolysis takes place under acidic conditions and is a procedure well documented in the art. See for example chapter 1 by J. F. W. Keana in "Steroid Reactions," edited by C. Djerassi, Holden Day (1963).

The $\Delta^{1,4}$ steroids may be prepared through the 3-ethylene ketal route by reacting the $\Delta^{4,9(11)}$-3-ethylene ketal with 2,3-dichloro-5,6-dicyanobenzoquinone (DDQ) according to the procedure discussed in chapter 6 or "Organic Reactions of Steroid Chemistry", supra, which is incorporated in pertinent part by reference herein.

The starting materials for the process aspects of this invention, namely those compounds represented by formulae (II), (IIB), (IIa) and (IIb), are known in the art and may be prepared according to representative preparations given hereafter.

Pharmaceutical Composition

The novel steroids of this invention may be formulated with suitable pharmaceutical vehicles known in the art to form particularly effective topical, anti-inflammatory compositions. Generally about 0.001 to about 10%w of the steroids defined hereinbefore are combined with about 90 to about 99.999%w suitable excipients which may include a pharmaceutically acceptable solvent and other pharmaceutically acceptable additives to form a pharmaceutical formulation which may be applied topically.

A pharmaceutically acceptable solvent is one which is substantially non-toxic and non-irritating under the conditions used and may be readily formulated into any of the classical drug formulations such as creams, ointments, lotions, gels, or the like. Particularly suitable solvents include water, glycerine, propylene carbonate, and glycol such as 1,2-propylene diol (i.e. propylene glycol), 1,3-propylene diol, or mixtures thereof; polyethylene glycol having a molecular weight of from 100 to 20,000; dipropylene glycol; etc.; and mixtures of the aforementioned with each other.

A cream, topical, anti-inflammatory mixture may be prepared as a semi-solid emulsion of oil in water or water in oil. A cream base formulation by definition is an emulsion which is a two phase system with one liquid (for example fats or oils) being dispersed as small globules in another substance (e.g. a glycol-water solvent phase which may be employed as the primary solvent for the novel steroids of this invention). Typically the cream formulation may contain other than the solvent with the steroids therein, fatty alcohols, surfactants, mineral oil or petrolatum and other typical pharmaceutical adjuvants such as anti-oxidants, antiseptics, or compatible adjuvants. A typical cream base formulation is given in the following table.

| | |
|---|---|
| Water/glycol mixture (15% or more glycol) | 50 - 99 |
| Fatty alcohol | 1 - 20 |
| Non-ionic Surfactant | 0 - 10 |
| Mineral Oil | 0 - 10 |
| Typical pharmaceutical adjuvants | 0 - 5 |
| *Active Ingredients | 0.001 - 10 |

The fatty alcohol, non-ionic surfactant, and other adjuvants are discussed in copending application U.S. Ser. No. 551,811 filed Feb. 21, 1975 and as much of that application as is pertinent is incorporated herein by reference.

The novel steroids of this invention may also be formulated as ointments. A "classical" ointment is a semi-solid anhydrous composition which may contain mineral oil, white petrolatum, a suitable solvent such as a glycol and may include propylene carbonate and other pharmaceutically suitable additives such as surfactants, for example Span and Tween or wool fat (lanolin), along with stabilizers such as antioxidants and other adjuvants as mentioned before. Following is an example of a typical "classical" ointment base:

| | |
|---|---|
| White petrolatum | 40 - 94 |
| Mineral Oil | 5 - 20 |
| Glycol solvent | 1 - 15 |
| Surfactant | 0 - 10 |
| Stabilizer | 0 - 10 |
| Active Ingredients | 0.001 - 10.0 |

Other suitable ointment base formulations which contain propylene carbonate are described in a copending U.S. Pat. applications Ser. No. 85,246, filed Oct. 29, 1970 by Shastri et al. entitled "Propylene Carbonate Ointment Vehicle" and 201,997, filed Nov. 24, 1971 by Chang et al. entitled "Fatty Alcohol-Propylene Carbonate-Glycol Solvent Cream Vehicle". As much of those applications as is pertinent is incorporated herein by reference. Following is an ointment base formulation containing propylene carbonate found to be particularly effective for the compositions of this invention:

| | |
|---|---|
| Active Ingredients | 0.001 - 10.0 |
| Propylene Carbonate | 1 - 10 |
| Solvent | 1 - 10 |
| Surfactant | 1 - 10 |
| White Petrolatum | 70 - 97 |

Suitable solvents, surfactants, stabilizers, etc. are discussed in U.S. Ser. No. 551,811 and such discussion is incorporated herein by reference.

A suitable "non-classical" anhydrous, water washable "ointment type" base is described in U.S. Pat. No. 3,592,930 to Katz and Neiman, and as much of that disclosure as is pertinent is incorporated herein by reference. A representative composition of this invention utilizing such a base is as follows:

| | |
|---|---|
| Glycol solvent | 40 - 85 |
| Fatty alcohol | 15 - 45 |
| Compatible plasticizer | 0 - 15 |
| Compatible coupling Agent | 0 - 15 |
| Penetrant | 0 - 20 |
| Active Ingredients | 0.001 - 10.0 |

The fatty alcohols which are suitable have been previously disclosed above in this specification and in U.S. Pat. No. 3,592,930. As much of those disclosures as is pertinent is incorporated herein by reference.

Method of Treatment

Generally an inflamed condition in animals, particularly humans, is treated by contacting the inflamed area with an effective amount of the novel steroids of this invention, i.e. an amount sufficient to effect improvement of the inflamed condition. Preferably the steroids are first formulated to prepare a suitable pharmaceutical formulation, as discussed hereinbefore, which is then placed in contact with the inflamed area. An effective amount will depend upon the particular condition and the animal receiving the treatment but will vary between 0.001 to 5% by weight of the pharmaceutical composition and preferably will be between 0.01 and 1% by weight of the formulation. Using these levels in the formulation, a therapeutically effective and non-toxic amount, i.e. enough to effect an anti-inflammatory response, but not enough to harm the recipient, is applied to the inflamed area.

PREPARATION A

This Preparation sets forth a process for making a starting material of formula (II) wherein X is H. The Preparation is based on the method set forth in U.S. Pat. No. 3,053,838 to Fried. The compound 21-hydroxy-16α-17α-isopropylidenedioxypregna-1,4,9(11)-triene-3,20-dione (a known compound, see M. Heller, R. H. Lenhard, S. Bernstein, "Steroids" 5, 615–35, 1965) is reacted with mesyl chloride in the presence of an organic base such as pyridine to form the corresponding 21-mesyl steroid. This, in turn, is heated with potassium fluoride in ethylene glycol to form 21-fluoro-16α-17α-isopropylidenedioxypregna-1,4,9(11)-triene-3,20-dione.

PREPARATION B

A starting material of formula (II) wherein X is fluoro is known and may be prepared as taught in U.S. Pat. No. 3,409,613 issued Nov. 5, 1968 to J. H. Fried.

PREPARATION C

A starting material of formula (II) wherein X is chloro is prepared by following the procedure set forth in Preparation A but starting with 6α-chloro-21- hydroxy-16α,17α-isopropylidenedioxypregna-1,4,9(11)-triene-3,20-dione. This compound is prepared from 21-hydroxy-16α,17α-isopropylidenedioxypregna-4,9(11)-diene-3,20-dione (a known compound which may be prepared by hydrogenating 21-hydroxy-16α,-17α-isopropylidenedioxypregna-1,4,9(11)-triene-3,20-dione with tris-(triphenylphosphine)chlororhodium in benzene and ethanol) according to a method described by Ringold et al. in J.A.C.S. 80, 6464 (1958). In the Ringold et al method, the corresponding 21-acetate of the 3-ethoxy-16α,17α-isopropylidenedioxypregna-3,5,9(11)-trien-20-one is first prepared which is then reacted with N-chloro succinimide to form the 6β-Cl-Δ$^{4,9,(11)}$ steroid. This, in turn, is converted to the 6α-chloro Δ$^{4,9(11)}$ steroid using hydrochloric acid/acetic acid. This compound is then reacted with selenium dioxide to give the corresponding Δ$^{1,4,9(11)}$ steroid. The 21-acetate is hydrolyzed to give the desired 21-hydroxy 6α-chloro Δ$^{1,4,9(11)}$ steroid.

PREPARATION D

The starting material of formula (IIB) wherein X is H is a known compound and may be prepared as taught in U.S. Pat. No. 3,167,546 issued Jan. 26, 1965 to Bernstein et al. or in J. Am.Chem. Soc. 81, 4962 (1959).

PREPARATION E

The starting material of formula (IIB) wherein X is F is prepared by reacting 6α-fluoro-16α,17α-isopropylidenedioxypregna-4,9(11)-diene-3,20-dione (a known compound, see U.S. Pat. No. 3,197,470 issued July 27, 1965 to Deghenghi et al.) with selenium dioxide as taught in Ringold et al. J.A.C.S. 80, 6464 (1958).

PREPARATION F

The starting material of formula (IIB) wherein X is Cl is prepared by reacting 16α,17α-isopropylidenedioxy-pregna-4,9(11)-diene-3,20-dione (a known compound, see British Pat. No. 881,501 issued Nov. 1, 1961 to American Cyanamid Corp.) according to the Ringold et al. process of Preparation C.

PREPARATION G

The starting 3-ethylene ketals represented by formulae (IIa) and (IIb) are readily prepared by reacting the starting material made according to Preparation A–F with hydrogen in the presence of tris-(triphenylphoshine) chlororhodium in a solvent of benzene and ethanol. The resulting 3-keto-Δ$^{4,9(11)}$ steroid is then reacted with a mixture of dry benzene, ethylene glycol and p-toluenesulfonic acid monohydrate at reflux conditions using a water separator. The reaction mixture is then washed with aqueous sodium bicarbonate solution and water, dried and evaporated to dryness to yield a compound represented by formulae (IIa) or (IIb) which is recrystallized from acetone:hexane.

The following non-limiting examples are set forth to more fully describe the process and compounds of the invention and to teach one of skill in the art how to make representative compounds. These examples are illustrative only and are not presented to limit the scope of the invention in any way.

EXAMPLE 1

This example illustrates a process for preparing 9α,11β-dichloro-21,21-difluoro-16α,17α-propylidenedioxypregna-1,4-diene-3,20-diones.

a. Formylation

A compound of formula (1) was formylated according to the following reaction scheme and procedure

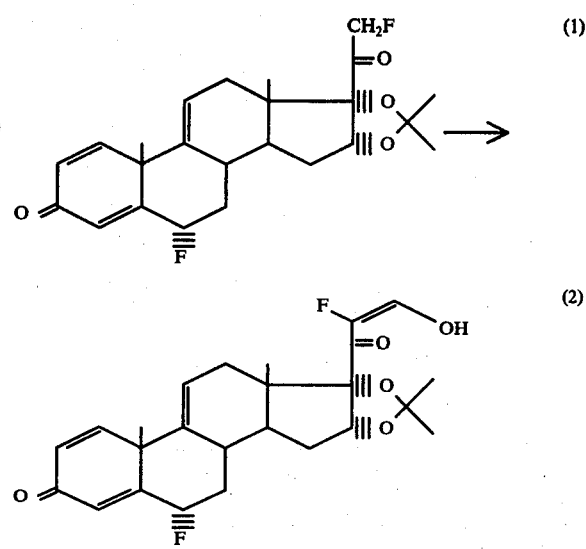

To an ice-cooled three neck flask equipped with a mechanical stirrer and charged with 5 milliliters (ml.) of freshly distilled isopropylcyclohexylamine and 50 ml. of dry tetrahydrofuran (THF), was added 20 ml. of 1.5 molar n-butyl lithium followed by a solution of 5.0 grams (g.) of the steroid (1) in 10 ml. of dry THF and 10 ml. of hexamethylphosphoric triamide (HMPA). After stirring under nitrogen at room temperature overnight, 5.0 ml. of purified ethyl formate was added and stirring continued for 4 more hours at room temperature. The contents of the flask were poured into 250 ml. of water and extracted with three 50 ml. portions of CH$_2$Cl$_2$. The combined CH$_2$Cl$_2$ layers were extracted with three 50 ml. portions of 1. N. NaOH solution which was combined with the previous aqueous layer. The combined aqueous basic layers were acidified with concentrated HCl in the presence of ice, and the white precipitate was extracted with CH$_2$Cl$_2$ (5×30 ml.). The combined CH$_2$Cl$_2$ extracts were washed with water, brine, dried over MgSO$_4$ and evaporated to give a yellow solid (6.25 g.). Recrystallization from acetone-hexane gave a crystalline sample, mp. 136°–138° C.

b. Chlorination and c. Deformylation

The compound of part (a), above is chlorinated and deformylated according to the following reaction scheme and procedure.

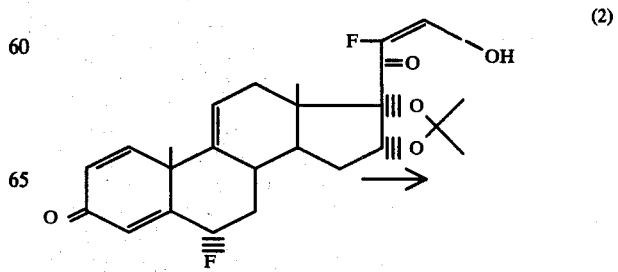

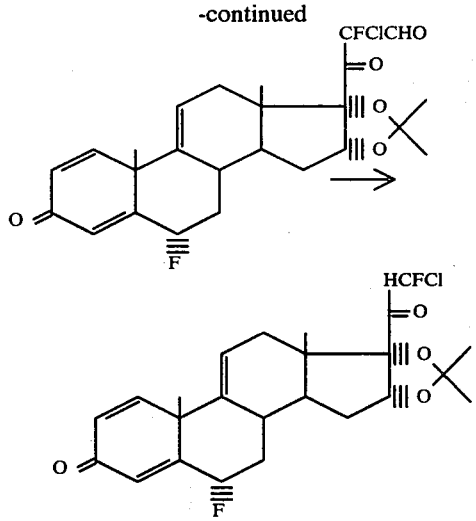

To a flask charged with 625 milligrams (mg.) of CuCl₂(3.6 millimole), 76.4 mg of LiCl (1.8 millimole) in 0.9 ml. of DMF was added 500 mg of the hydroxymethylene steroid (2). The solution was heated with stirring to 40°–50° C for 3 hours under N₂ then to 80° C for 1 hour. The solution was partitioned between CH₂Cl₂ (30 ml.) and water (50 ml.). After extracting the aqueous layer with CH₂Cl₂ (3×20 ml.) the combined organic layers were washed with water, dried over MgSO₄ and evaporated to give a solid (546 mg).

This crude solid was dissolved in ethanol (5 ml.) and cooled to 0° C. Barium hydroxide (500 mg) was added and the mixture was stirred at 0° C for 2 hours then partioned between 50 ml. ice cooled 0.1 N. HCl and CH₂Cl₂(30 ml.). After extracting the aqueous layer with CH₂Cl₂ (2×20 ml.) the combined organic layers were washed with water, brine, dried over MgSO₄ and evaporated to dryness to give a solid (496 mg.). Recrystallization from CH₂Cl₂ cyclohexane gave a crystalline sample, mp. 218°–222° C.

d. Fluorination

The compound of formula (3) was fluorinated to form the corresponding 6α,21,21-trifluoro compound according to the following reaction scheme and procedure:

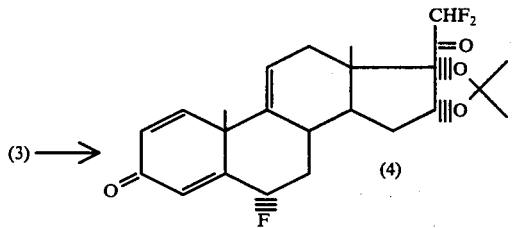

To a flask charged with 1.17 g of N(CH₃)₄F and 15 g of sulfolane and heated to 75° C was added with stirring 550 mg of the 21-chloro-21-fluoro steroid (3). The solution was stirred under nitrogen (N₂) for about ½ hour maintaining the temperature at 75° C. The contents of the flask were poured into 50 ml. water, and extracted with three 50 ml portions benzene. The combined benzene layers were washed with water, brine, dried over MgSO₄ and evaporated to give 600 mg of a brown solid which was purified by chromatography on 50 g of silica gel with ethyl acetate and hexane as eluting solvents, giving 314 mg. of the pure crystalline product, mp. 223°–224° C.

e. Dichlorination at 9α/11β

The compound of formula (4) was dichlorinated to form a product of formula (5) according to the following reaction scheme and procedure:

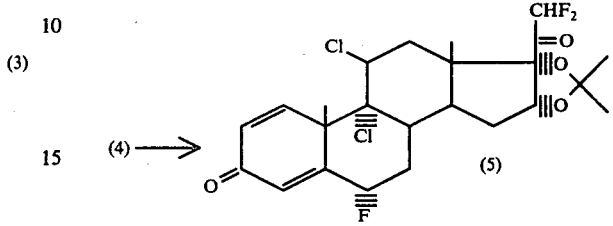

The 21,21-difluoro steroid (4) (45 mg) was dissolved in 2 ml of a solution made by adding 1 ml of pyridine to 10 ml of CH₂Cl₂. A stream of chlorine gas was bubbled through this solution for 4 minutes. After diluting with 20 ml of CH₂Cl₂ this solution was washed with dilute HCl, water, brine, dried over MgSO₄ and evaporated to give a solid (52 mg). The product was purified by preparative thick layer chromatography on silica gel with ethyl acetate in hexane as developing solvent. Recrystallization from acetone hexane gave the analytical sample (24 mg), of 9α,11β-dichloro-6α,21,21-trifluoro-16α,-17α-isopropylidenedioxypregna-1,4-diene-3,20-dione; mp. 240°–245° C (decomposed).

Similarly, by following steps (a) through (e) in this example but substituting
  6α-chloro-16α,17α-isopropylidenedioxypregna-
    1,4,9(11)-triene-3,20-dione and
  21-fluoro-16α,17α-isopropylidenedioxypregna-
    1,4,9(11)-triene-3,20-dione for 6α,21-difluoro-16α,-17α-isopropylidenedioxypregna-1,4,9(11)-triene-3,20-dione (formula 1) in step (a) the corresponding 6α-chloro and 6α-hydrogen compounds of this invention may be obtained.

EXAMPLE 2

This example illustrates the preparation of 9α,11β,21-trichloro-21-fluoro-16α,17α-isopropylidenedioxypregna-1,4-diene-3,20-diones.

a. Formylation, b. Chlorination, and c. Deformylation

The procedure set forth in Example I, step (a)–(c) was followed to obtain 21-chloro-6α,21-difluoro-16α,-17α-isopropylidenedioxypregna-1,4,9(11)-triene-3,20-dione. The resulting compound is treated according to the procedure of Example I, step (e) to give 9α,11β,21-trichloro-6α,21-difluoro-16α,17α-isopropylidenedioxypregna-1,4-diene-3,20-dione.

Similarly, by following the above procedure of this example but substituting
  6α-chloro-21-fluoro-16α,17α-isopropylidenedioxy-
    pregna-1,4,9(11)-triene-3,20-dione and
  21-fluoro-16α,17α-isopropylidenedioxypregna-
    1,4,9(11)-triene-3,20-dione for 6α,21-difluoro-16α,-17α-isopropylidenedioxypregna-1,4,9(11)-triene- 3,20-dione (formula 1) of step (a), the corresponding 6α,-chloro and 6α-hydrogen compounds of this invention may be obtained.

EXAMPLE 3

This example sets forth a process for preparing 21-chloro-9α,21-difluoro-11β-hydroxy-16α,17α-isopropylidenedioxypregna-1,4-diene-3,20-dione of this invention.

The compound represented by formula (3) was prepared as in Example I, steps (a)–(c). The compound, 21-chloro-9β,11β-oxido-6α,21-difluoro-16α,17α-isopropylidenedioxypregna-1,4-diene-3,20-dione, was prepared according to the following reaction scheme and procedure:

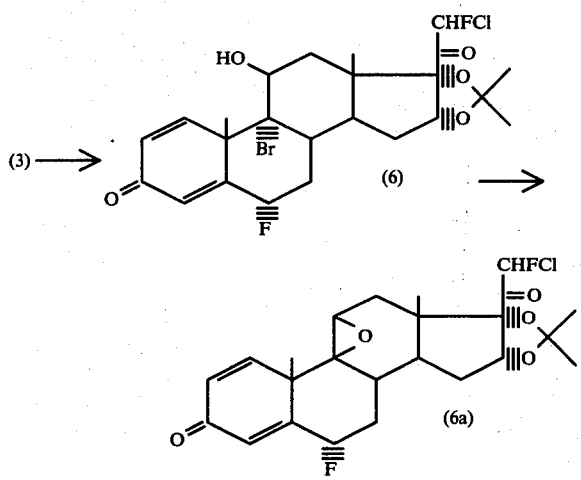

A solution of the 21-chloro-21-fluoro steroid (3) (106 mg) in dioxane (1.2 ml) was cooled to 10° C. Dibromantin (160 mg) was added, followed by 0.09 ml of a solution made by diluting 3 ml of 30% HClO₄ to 27 ml with water. The temperature was maintained at 10° C for 4 hours with stirring.

To the above solution was added 2.3 ml of isopropyl alcohol followed by 255.6 mg of potassium acetate (KOAC). The solution was heated at reflux overnight. The reaction mixture was then poured into 100 ml of water, extracted with 80 ml of benzene and chloroform (3×10 ml). The combined organic layers were washed with water (100 ml), NaHCO₃ (50 ml) and brine (50 ml), dried over MgSO₄ and evaporated to dryness. The crystalline residue (176 mg) was recrystallized from methanol to give the 9β,11β-oxido derivative (6α), mp. 208° C.

The 9β,11β-oxido compound represented by formula (6) was then hydrofluorinated to give a compound of this invention according to the following reaction scheme and procedure.

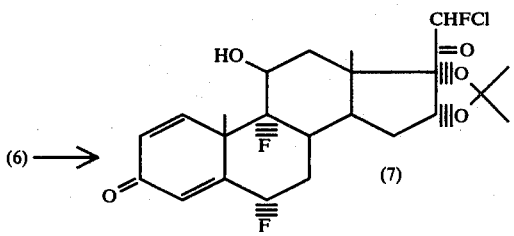

Eight-tenths (0.8) ml. of a hydrogen fluoride-urea complex was added to a sample of the epoxy steroid (6) (52 mg.) in a polyethylene bottle. The reaction mixture was stirred at room temperature for 3 hours and then poured into an ammonium hydroxide solution, (0.1 N., 20 ml.). The product was extracted with three 120 ml. portions of CH₂Cl₂ and the combined CH₂Cl₂ extracts were washed with water, brine, dried over MgSO₄ and evaporated to give a solid (35 mg.). Recrystallization from ethanol gave 21-chloro-6α,9α,21-trifluoro-11β-hydroxy-16α,17α-isopropylidenedioxypregna-1,4-diene-3,20-dione, mp. 303° C (decomposed).

Similarly by following the procedure of this example but substituting for the compound represented by formula (3), the following compounds:

6α,21-dichloro-21-fluoro-16α,17α-isopropylidenedioxypregna-1,4,9(11)-triene-3,20-dione;

21-chloro-21-fluoro-16α,17α-isopropylidenedioxypregna-1,4,9(11)-triene-3,20-dione, the corresponding compounds of this invention may be obtained.

EXAMPLE 4

This example sets forth a process for preparing 9α,21,21-trifluoro-11β-hydroxy-16α,17α-isopropylidenedioxypregna-1,4-diene-3,20-diones.

The compound represented by formula (4), namely 6α,21,21-trifluoro-16α,17α-isopropylidenedioxypregna-1,4,9(11)-triene-3,20-dione, was prepared as in Example 1, steps (a)–(d). The 9β,11β-epoxidation and subsequent hydrofluorination procedure set forth in Example 3 was followed to prepare 6α,9β,21,21-tetrafluoro-11β-hydroxy-16α,17α-isopropylidenedioxypregna-1,4-diene-3,20-dione.

Similarly, by following the process of this example but substituting 6α-chloro-21,21-difluoro-16α,17α-isopropylidenedioxypregna-1,4,9(11)-triene-3,20-dione and 21,21-difluoro-16α-17α-isopropylidenedioxypregna-1,4,9(11)-triene-3,20-dione, for the compound represented by formula (4), the corresponding 6α-chloro or 6α-hydrogen compounds of this invention may be obtained.

EXAMPLE 5

This example sets forth a procedure for preparing the 9α-bromo-11β-hydroxy Δ¹,⁴ steroids of this invention. In this process, the procedure for preparing a compound represented by formula (6) is followed, and after the compound represented by formula (3) was reacted with dibromantin and HClO₄ for 4 hours at 10° C, the reaction mixture is poured into ice water then extracted with methylene chloride. The organic phase is washed with water, aqueous NHCO₃ and dried over MgSO₄. The solvent is then evaporated and the product is recrystallized from ethanol to give 9α-bromo-21-chloro-6α,21-difluoro-11β-hydroxy-16α,17α-isopropylidenedioxypregna-1,4-diene-3,20-dione m.p. 218°–220° C (decomposed).

Similarly by following the above procedure but substituting 6α,21-dichloro-21-fluoro-16α,17α-isopropylidenedioxypregna-1,4,9(11)-triene-3,20-dione and 21-chloro-21-fluoro-16α,17α-isopropylidenedioxypregna-1,4,9(11)-triene-3,20-dione for the compound of formula (3), the corresponding 6α-chloro and 6α-hydrogen compounds are obtained.

EXAMPLE 6

By following the procedure of Example 5 but substituting

6α,21,21-trifluoro-16α,17α-isopropylidenedioxypregna-1,4,9(11)-triene-3,20-dione, 6α-chloro-21,21-difluoro-16α,17α-isopropylidenedioxypregna-1,4,9(11)-trine-3,20-dione, 21,21-difluoro-16α,17α-isopropylidenedioxypregna-1,4,9(11)-triene-3,20-dione for the compound represented by formula (3), other corresponding compounds of this invention may be obtained.

EXAMPLE 7

This example sets forth a procedure for preparing a 9α-H-11β-OH Δ¹,⁴ steroid of this invention according to the following reaction scheme and procedure:

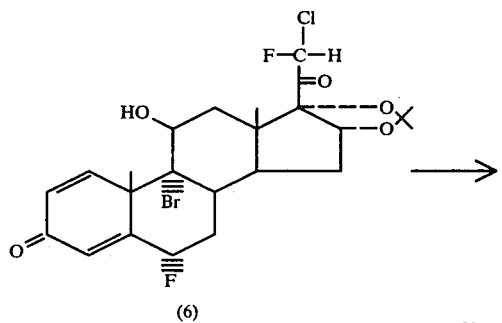

(6)

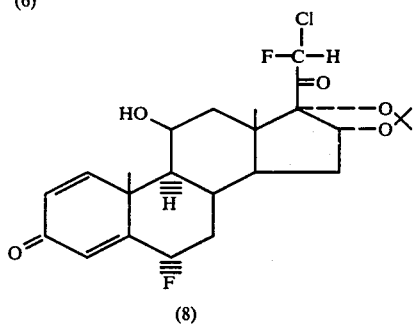

(8)

To a flask charged with 31 mg. of tributyltin hydride in 15 ml. of freshly distilled THF is added 50 mg. of the steroid (6). A trace amount of azobisisobutyronitrile is added to the vigorously stirred solution and the reaction flask is irradiated with a lamp. After ½ hour the solvent is removed under vacuum and the product is extracted with 50 ml. of CH₂Cl₂. The organic solution is washed with water, brine, dried over MgSO₄ and evaporated to dryness to give a solid. Recrystallization from MeOH gave a crystalline product of 21-chloro-6α,21-difluoro-11β-hydroxy-16α,17α-isopropylidenedioxypregna-1,4-diene-3,20-dione.

Similarly, by substituting other 9α-Br-11β-OH-Δ¹,⁴ steroids prepared according to Example 5 and Example 6, for the compound represented by formula (6), other 9α-H-11β-OH-Δ¹,⁴ compounds of this invention may be prepared which correspond to the respective starting compounds.

EXAMPLE 8

The 9α-chloro-11β-OH-Δ¹,⁴ steroids of this invention may be prepared by reacting a 9,11-oxido compound prepared according to Examples 3 and 4 with hydrogen chloride by well known procedures and isolated by procedures discussed hereinbefore.

EXAMPLE 9

This example sets forth a process for preparing the 9α,11β,21,21-tetrachloro-Δ¹,⁴ steroids of this invention according to the following procedure. Five g. of 6α-fluoro-16α,17α-isopropylidenedioxypregna-1,4,9(11)-triene-3,20-dione is formylated according to the procedure set forth in Example 1 except that once the ethyl formate is added stirring is continued at refluxing temperature for four more hours. After extraction and isolation, recrystallization from acetone gave the corresponding 21-hydroxymethylene compound, m.p. 201.5°–203° C. This product was chlorinated and deformylated according to the procedure of Example 1 to give 21,21-dichloro-6α-fluoro-16α,17α-isopropylidenedioxypregna-1,4,9(11)-triene-3,20-dione having a m.p. of 199°–200° C. By following the dichlorination step of part (e) in Example I, 9α,11β,21,21-tetrachloro-6α-fluoro-16α,17α-isopropylidenedioxypregna-1,4-diene-3,20-dione, m.p. 225°–235° C (dec.), is prepared.

Similarly, by substituting the appropriate 6α-chloro or 6α-H starting material for the 6α-F-Δ¹,⁴,⁹⁽¹¹⁾ steroid in this example, other corresponding compounds of this invention are prepared.

EXAMPLE 10

This example sets forth a process for preparing the 9α-fluoro-11β-hydroxy-21,21-dichloro-Δ¹,⁴ steroids of this invention. The formulation, chlorination and deformylation steps of Example 9 are followed and the 21,21-dichloro-Δ¹,⁴,⁹⁽¹¹⁾ steroid thus obtained is reacted according to the sequence of Example 3 to give the corresponding 21,21-dichloro 9α,11β-bromohydrin and subsequent 9,11-oxido steroid (m.p. 212° C-dec.) which in turn is reacted with hydrogen fluoride as taught in Example 3 to give 21,21-dichloro-6α,9α-difluoro-11β-hydroxy-16α,17α-isopropylidenedioxypregna-1,4-diene-3,20-dione, m.p. 270°–285° C (dec.).

Similarly, the corresponding 6α-chloro and 6α-hydrogen compound are prepared by employing the appropriate starting material.

The intermediate 21,21-dichloro-9α,11β-bromohydrins are prepared according to the process of Example 5 while the 9α-hydrogen-11β-hydroxy compounds are prepared according to Example 7. The corresponding 21,21-dichloro-9α-Cl-11β-OH-Δ¹,⁴ steroids are prepared by following the procedures of Example 8.

EXAMPLE 11

The 21,21-dibromo compounds of this invention may be prepared by following the procedures of Examples 9 and 10 but dibrominating at 21 instead of dichlorinating.

EXAMPLE 12

The example sets forth a process for making the Δ⁴ steroids of this invention.

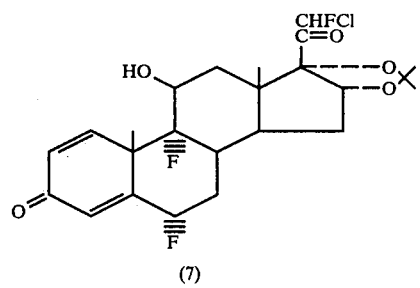

(7)

A solution of 25 mg. of tris-(triphenylphosphine) chlororhodium in 6 ml. of benzene and 15 ml.. of ethanol is stirred under hydrogen for 60 min. The above steroid (244 mg.) is added and the resulting solution is stirred under hydrogen at room temperature and atmospheric pressure. After hydrogen uptake is complete, the solution is evaporated to dryness and the residue taken up in a mixture of petroleum ether and methylene chloride. The pure product corresponding to the $\Delta^{1,4}$ compound (7), above, is isolated by column chromatography on silica gel.

Similarly, by substituting other $\Delta^{1,4}$ steroids of this invention made according to Examples 1-11 for the compound of formula (7), other corresponding $\Delta^4$ steroids are prepared.

We claim as our invention:

1. A compound chosen from those represented by the formula

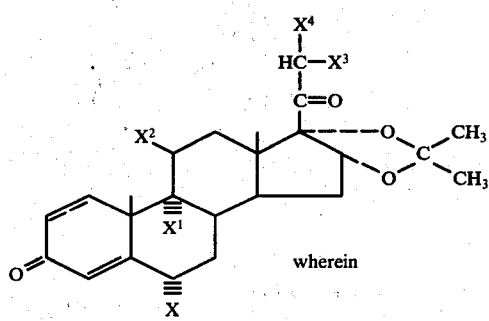

wherein

X is hydrogen, fluoro, or chloro;
$X^1$ is hydrogen, fluoro, chloro or bromo;
$X^2$ is hydroxy or may be chloro when $X^1$ is chloro;
$X^3$ and $X^4$ are independently fluoro, chloro or bromo; and
the broken line between C-1 and C-2 indicates that the bond between C-1 and C-2 is a single or a double bond.

2. The compound of claim 1 wherein $X^3$ and $X^4$ are independently fluoro or chloro.

3. The compound of claim 2 wherein X, $X^1$, $X^3$ and $X^4$ are all fluoro; $X^2$ is hydroxy; and the bond between C-1 and C-2 is a double bond; namely $6\alpha,9\alpha,21,21$-tetrafluoro-$11\beta$-hydroxy-$16\alpha,17\alpha$-isopropylidenedioxypregna-1,4-diene-3,20-dione.

4. The compound of claim 2 wherein $X^4$ is chloro; X, $X^1$ and $X^3$ are all fluoro; $X^2$ is hydroxy; and the bond between C-1 and C-2 is a double bond; namely, 21-chloro-$6\alpha,9\alpha,21$-trifluoro-$11\beta$-hydroxy-$16\alpha,17\alpha$-isopropylidenedioxypregna-1,4-diene-3,20-dione.

5. The compound of claim 2 wherein $X^1$, $X^2$ and $X^3$ are all chloro; X and $X^4$ are each fluoro; and the bond between C-1 and C-2 is a double bond; namely, $9\alpha,11\beta,21$-trichloro-$6\alpha,21$-difluoro-$16\alpha,17\alpha$-isopropylidenedioxypregna-1,4-diene-3,20-dione.

6. The compound of claim 2 wherein $X^1$ and $X^2$ are each chloro; X, $X^3$ and $X^4$ are all fluoro; and the bond between C-1 and C-2 is a double bond; namely, $9\alpha,11\beta$-dichloro-$6\alpha,21,21$-difluoro-$16\alpha,17\alpha$-isopropylidenedioxypregna-1,4-diene-3,20-dione.

7. A process for preparing 21,21-dihalosteroids which process comprises a. reacting a formylating agent with a compound represented by the formula

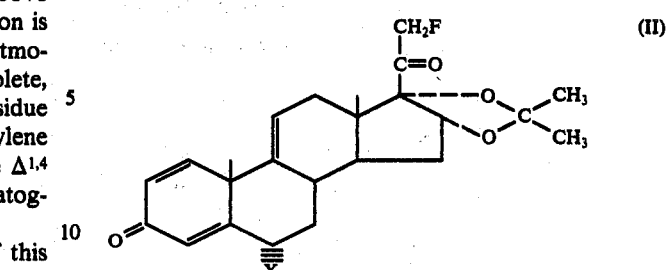

wherein X is fluoro, chloro, or hydrogen to form a compound represented by the formula

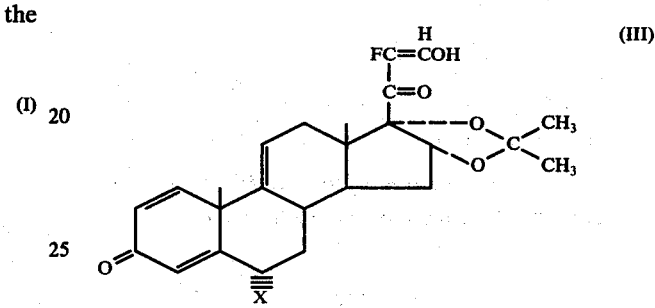

wherein X is previously defined;

b. reacting the compound represented by formula (III) of this claim with a brominating or chlorinating agent to form a compound represented by the formula

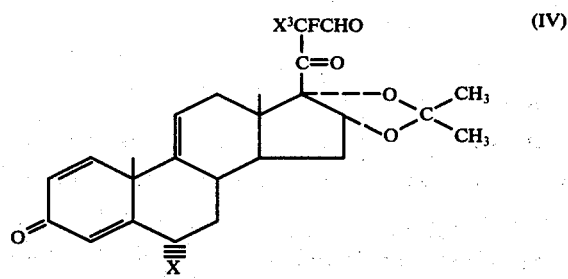

wherein X is previously defined and
$X^3$ is chloro or bromo; and c. reacting the compound represented by formula (IV) with a deformylating agent to form a compound represented by the formula

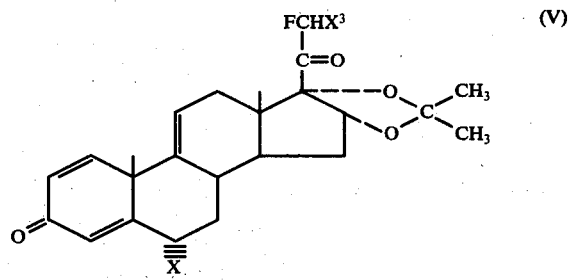

wherein X and $X^3$ are defined previously.

8. The process of claim 7 wherein said chlorinating agent is chlorine and $X^3$ is chloro.

9. The process of claim 8 wherein d. the compound represented by formula (V) is epoxidized to form a compound represented by the formula

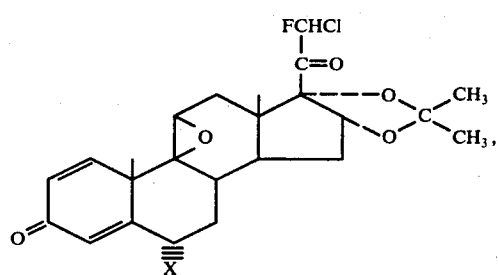

(VI)

wherein X is previously defined and e. the compound represented by formula (VI) is reacted with a hydrofluorinating agent to form a compound represented by the formula

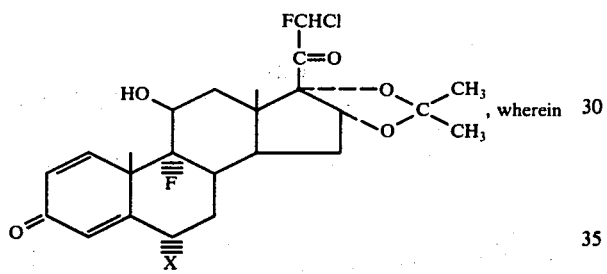

, wherein

X is defined previously.

10. The process of claim 9 wherein the compound prepared in step (e) is reduced to form the corresponding $\Delta^4$ steroid.

11. The process of claim 7 wherein the compound represented by formula (V) is reacted with a chlorinating agent to form a 9α,11β,21-trichloro $\Delta^{1,4}$-steroid represented by the formula

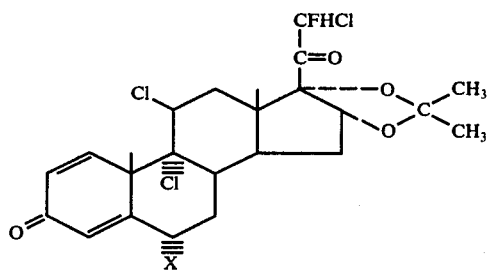

wherein X is defined previously.

12. The process of claim 11 wherein said trichloro $\Delta^{1,4}$-steroid is reduced to form the corresponding $\Delta^4$ steroid of the formula.

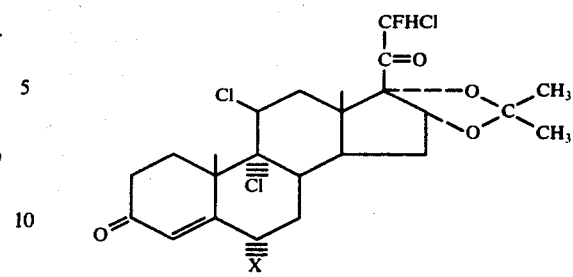

13. The process of claim 7 wherein $X^3$ is chloro and said compound represented by formula (V) is reacted with a fluorinating agent to form a compound represented by formula

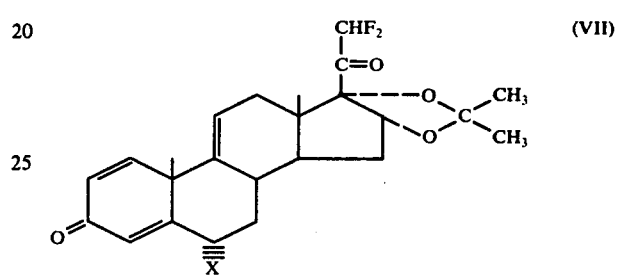

(VII)

wherein X is defined previously.

14. The process of claim 13 wherein the compound of Formula (VII) is chlorinated to form a 9α,11β-dichloro steroid represented by the formula

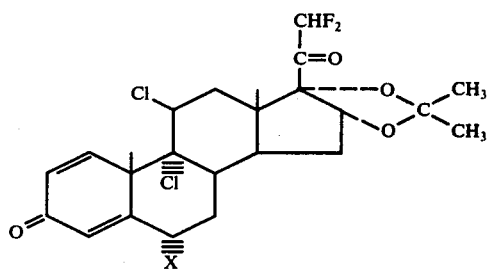

wherein X is defined previously.

15. The process of claim 14 wherein said 9α,11β-dichloro-$\Delta^{1,4}$ steroid is reduced to form the corresponding $\Delta^4$ steroid of the formula.

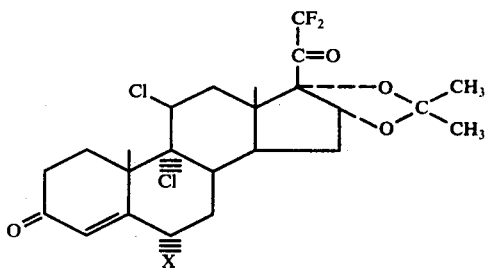

16. The process of claim 13 wherein the compound represented by formula (VII) is epoxidized to form a compound represented by

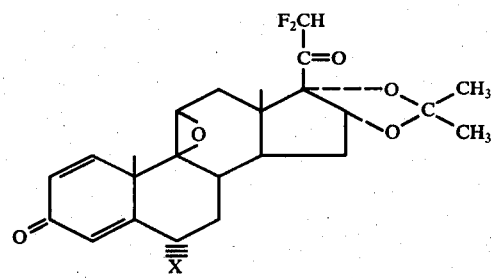

wherein X is previously defined and reacting said compound represented by formula (VIII) with a hydrofluorinating agent to form a 9α,21,21-trifluoro Δ¹,⁴-steroid represented by

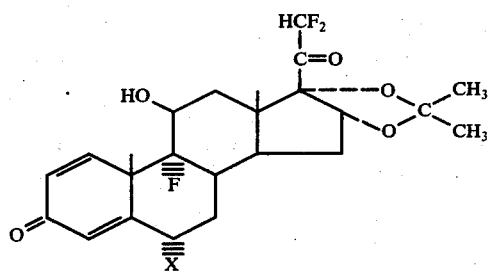

wherein X is previously defined.

17. The process of claim 16 wherein said 9α,21,21-trifluoro Δ¹,⁴-steroid is reduced to form the corresponding Δ⁴-steroid of the formula.

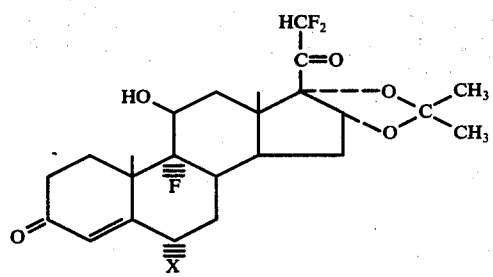

18. A topical anti-inflammatory, composition which comprises a compound of claim 1 formulated with a suitable pharmaceutical vehicle.

19. A topical anti-inflammatory composition which comprises a compound of claim 2 formulated with a suitable pharmaceutical vehicle.

20. A method of treating an inflamed condition in animals which comprises contacting the inflamed area on said animal with a therapeutically effective amount of a compound of claim 1.

21. A method of treating an inflamed condition in animals which comprises contacting the inflamed area on said animal with a therapeutically effective amount of a compound of claim 2.

22. The compound of claim 2 wherein X and X³ are each fluoro, X¹ is bromo, X² is hydroxy, X⁴ is chloro and the bond between C-1 and C-2 is a double bond; namely, 9α-bromo-21-chloro-6α,21-difluoro-11β-hydroxy-16α,17α-isopropylidenedioxypregna-1,4-diene-3,20-dione.

23. The compound of claim 2 wherein X, X³ and X⁴ are each fluoro, X¹ is bromo, X² is hydroxy and the bond between C-1 and C-2 is a double bond; namely, 9α-bromo-6α,21,21-trifluoro-11β-hydroxy-16α,17α-isopropylidenedioxypregna-1,4-diene-3,20-dione.

24. The compound of claim 2 wherein X is fluoro; X¹, X², X³ and X⁴ are each chloro; and the bond between C-1 and C-2 is a double bond; namely, 9α,11β,21-21-tetrachloro-6α-fluoro-16α,17α-isopropylidenedioxypregna-1,4-diene-3,20-dione.

25. The compound of claim 2 wherein X and X¹ are fluoro, X² is hydroxy, X³ and X⁴ are each chloro and the bond between C-1 and C-2 is a double bond; namely 21,21-dichloro-6α,9α-difluoro-11β-hydroxy-16α,17α-isopropylidenedioxypregna-1,4-diene-3,20-dione.

26. A process for preparing 21,21-dihalosteroids which process comprises
a. reacting a formylating agent with a compound represented by the formula

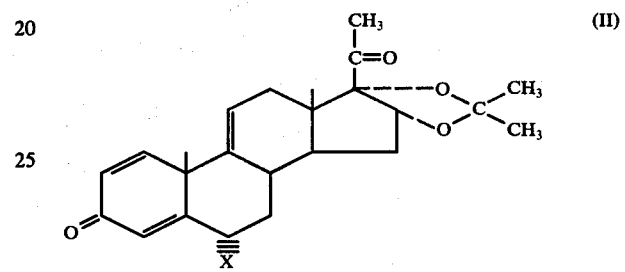

wherein X is fluoro, chloro, or hydrogen, to form a compound represented by the formula

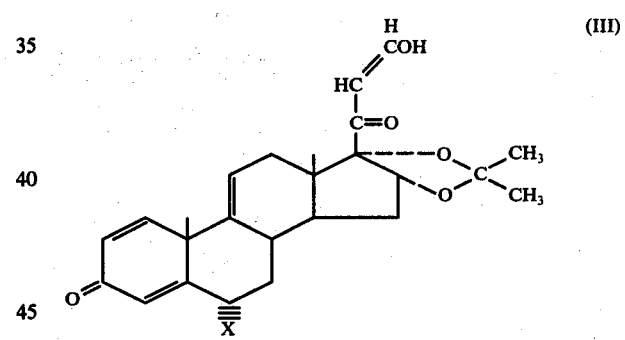

wherein X is previously defined;

b. reacting the compound represented by formula (III) of this claim with a brominating or chlorinating agent to form a compound represented by the formula

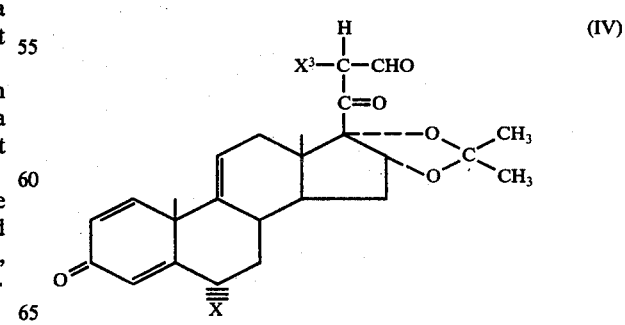

wherein X is previously defined and
X³ is chloro or bromo;

c. reacting the compound represented by formula (IV) with a brominating or chlorinating agent to form a compound represented by the formula

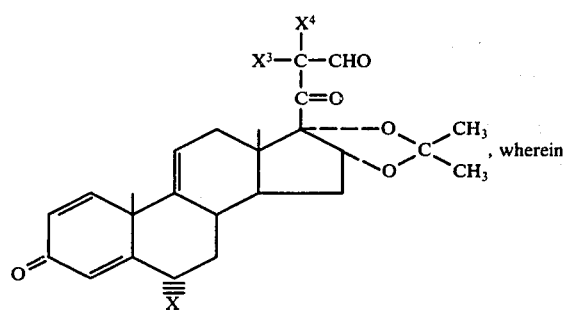

wherein X and $X^3$ are defined previously and $X^4$ is bromo or chloro; and d. reacting the compound of step (c) with a deformylating agent to form a compound represented by the formula

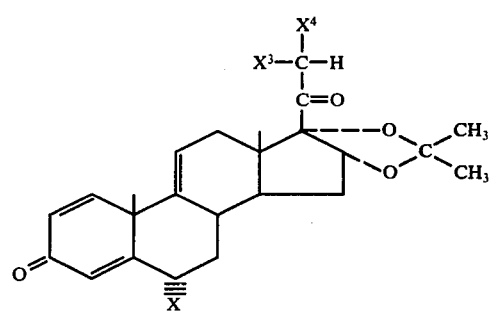
(V)

wherein X and $X^3$ are defined previously in this claim.

27. The process of claim 26 wherein $X^3$ and $X^4$ are both chloro.

28. The process of claim 27 wherein e. the compound represented by formula (V) is epoxidized to form a compound represented by the formula

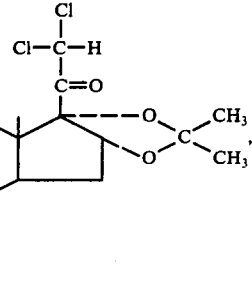
(VI)

wherein X is as defined in claim 26 and f. the compound represented by formula (VI) is reacted with a hydrofluorinating agent to form a compound represented by the formula

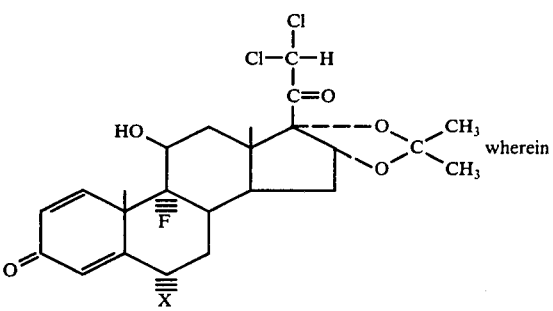

X is defined in claim 26.

29. The process of claim 26 wherein the compound represented by the formula (V) is reacted with a chlorinating agent to form a $9\alpha,11\beta$-dichloro $\Delta^{1,4}$-steroid represented by the formula

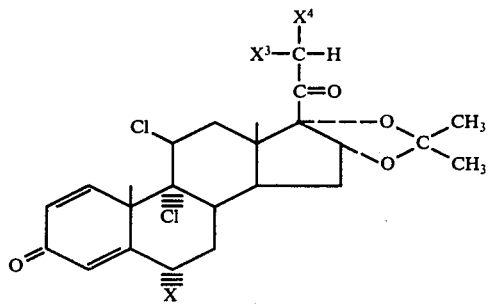

wherein X, $X^3$ and $X^4$ are defined as in claim 26.

* * * * *